(12) United States Patent
Juarez Molina et al.

(10) Patent No.: US 12,426,600 B2
(45) Date of Patent: Sep. 30, 2025

(54) *METHYLOBACTERIUM* sp. nov. STRAIN, COMPOSITIONS COMPRISING IT, AND ITS USE AS BIO-STIMULANT AND ENDOPHYTE NITROGEN-FIXING BACTERIUM

(71) Applicant: SYMBORG, SL, Murcia (ES)

(72) Inventors: Jesus Juarez Molina, Murcia (ES); Felix Fernandez Martin, Murcia (ES); Antonio Jose Bernabe Garcia, Murcia (ES); Ana Vila Martinez, Murcia (ES); Francisco Jose Carmona Alvarez, Murcia (ES); Rocio Torres Vera, Murcia (ES)

(73) Assignee: CORTEVA AGRISCIENCE LLC, Indianapolis, IN (US)

( * ) Notice: Subject to any disclaimer, the term of this patent is extended or adjusted under 35 U.S.C. 154(b) by 836 days.

(21) Appl. No.: 17/616,346

(22) PCT Filed: May 7, 2020

(86) PCT No.: PCT/IB2020/054319
§ 371 (c)(1),
(2) Date: Dec. 3, 2021

(87) PCT Pub. No.: WO2020/245675
PCT Pub. Date: Dec. 10, 2020

(65) Prior Publication Data
US 2022/0248684 A1    Aug. 11, 2022

(30) Foreign Application Priority Data

Jun. 3, 2019 (EP) .................................. 19382457

(51) Int. Cl.
*A01N 63/20* (2020.01)
*C05F 11/08* (2006.01)
*C12N 1/20* (2006.01)
*C12N 1/32* (2006.01)
*C12R 1/01* (2006.01)

(52) U.S. Cl.
CPC .............. *A01N 63/20* (2020.01); *C05F 11/08* (2013.01); *C12N 1/205* (2021.05); *C12N 1/32* (2013.01); *C12R 2001/01* (2021.05)

(58) Field of Classification Search
CPC .......... A01N 63/20; C12N 1/205; C12N 1/32; C05F 11/08; C12R 2001/01
See application file for complete search history.

(56) References Cited

U.S. PATENT DOCUMENTS

2015/0101373 A1    4/2015    Munusamy et al.
2018/0168167 A1    6/2018    Juarez et al.

FOREIGN PATENT DOCUMENTS

KR    20070106867 A    11/2007

OTHER PUBLICATIONS

Siwon Lee, et al; *Methylobacterium dankookense* sp. nov. isolated from drinking water; The Journal of Microbiology; vol. 47; No. 6; Dec. 2009; pp. 716-720; XP055350364.
International Search Report and Written Opinion for PCT/IB2020/054319 dated Jun. 5, 2020.

*Primary Examiner* — Danah Al-Awadi
*Assistant Examiner* — John W Lippert, III
(74) *Attorney, Agent, or Firm* — LUCAS & MERCANTI, LLP

(57) ABSTRACT

A *Methylobacterium* sp. nov. strain, deposited under accession number CECT 9580, to compositions comprising it, and its use as bio-stimulant and endophyte nitrogen-fixing bacterium in plants.

17 Claims, 8 Drawing Sheets

METHYLOBACTERIUM sp. nov. STRAIN, COMPOSITIONS COMPRISING IT, AND ITS USE AS BIO-STIMULANT AND ENDOPHYTE NITROGEN-FIXING BACTERIUM

CROSS REFERENCE TO RELATED APPLICATION

This Application is a 371 of PCT/IB2020/054319 filed on May 7, 2020, which claims priority of European Patent Application No. 19382457.0 filed Jun. 3, 2019, both of which are incorporated herein by reference.

FIELD OF THE INVENTION

The present invention relates to the agronomic field. Specifically, it relates to a *Methylobacterium* sp. nov. strain, to compositions comprising it, and to its use as bio-stimulant and endophyte nitrogen-fixing bacterium in plants.

BACKGROUND ART

Many fertilizers are known in the field of agriculture. In particular, nitrogen-based fertilizers, such as, ammonia, ammonium nitrate ($NH_4NO_3$) and urea, are commonly used in order to maintain the crop yield as high as possible. In fact, many biological processes in plants involve nitrogen; for example, nitrogen is involved in the production of amino acids and, therefore, proteins.

However, only a fraction of the nitrogen-based fertilizers that are applied to crops is converted to plant matter. The amount of fertilizer that is not converted into plant matter may accumulate in the soil or may flow out into surface water, or groundwater, thereby causing water pollution.

In order to reduce chemical fertilizers usage, inoculants including nitrogen-fixing bacteria may be used to partially replace such chemical fertilizers.

The main reservoirs of methylotrophic bacteria are, generally, soil and water (both sweet and salt), but these bacteria are also present in a wide variety of natural and artificial environments, including dust, lake sediments, air, facial creams, fermented products, water supply networks, bathrooms and air conditioning systems.

However, known inoculants do not allows a satisfactory results in plants' growth stimulation and also do not allow for the replacement of chemical fertilizers, nor for a significant reduction in the use of such chemical products.

Most of known microorganisms that act as growth stimulators and/or Nitrogen fixing are not able to produce a significant Nitrogen content in order to reduce significantly nitrogen units needed for plants growth. These known microorganisms produce some kinds of auxins, like indolacetic acid and promote rooting more that Nitrogen fixation.

US 2015/101373 A1 discloses nitrogen fixing and plant growth promoting *Methylobacterium* NRRL B-50628 and NRRL B-50629.

KR 2007 0106867 A discloses nitrogen fixing and plant growth promoting *Methylobacterium fujisawaense* CBMB 20.

US 2018/168167 A1 discloses plant growth promoting fungi *Glomus iranicum* var. tenuihypharum BCCM 54871.

SI-WON LEE ET AL: "*Methylobacterium dankookense* sp. nov., isolated from drinking water", THE JOURNAL OF MICROBIOLOGY, vol. 47, no. 6, (2009 Dec. 1), pages 716-720, XP055350364, DOI: 10.1007/s12275-009-0126-6, discloses enzymatic activity and genetical similarity of *Methylobacterium dankookense*.

SUMMARY OF THE INVENTION

An aim of the present invention is thus to provide a strain of *Methylobacterium* sp. nov., as well as compositions comprising it, to provide a positive impact to crops.

Another aim of the invention is to provide a strain of *Methylobacterium* sp. nov. which allows to at least reduce the usage of chemical nitrogen-based fertilizers.

These and other aims are achieved by the *Methylobacterium* sp. nov. strain according to claim 1.

DETAILED DESCRIPTION

In the following description, the features of the invention will be described with reference to exemplary embodiments; however, any feature of the invention disclosed herein, may be combined with one or more other features here disclosed to provide further embodiments of the present invention. Such embodiments shall be considered as disclosed by the present application.

An object of the present invention is thus a strain of *Methylobacterium* sp. nov., deposited under accession number CECT 9580.

The strain of *Methylobacterium* sp. nov. of the invention, identified by the depositor with the reference SB0023/3, was deposited on 21 Mar. 2018 at the International Depositary Authority Colección Española De Cultivos Tipo (CECT), Edificio 3 CUE, Parc Cientific Universitat de Valencia, Catedrático Agustin Escardino, 9, 46980 Paterna (Valencia) ESPAÑA, by Symborg S. L., with address Campus de Espinardo, 7, edificio CEEIM, 30100 Murcia, Spain, with the number CECT 9580.

The strain of the invention was isolated from the interior of the spores of the mycorrhizal fungus *Glomus iranicum* var. tenuihypharum. *Glomus iranicum* var. tenuihypharum is an arbuscular mycorrhizal fungus that is known per se in the art. *Glomus iranicum* var. tenuihypharum was deposited on 19 Apr. 2013, under BCCM deposit number 54871, at the international depositary authority Belgian Coordinated Collections of Micro-Organisms (BCCM) with the address at Université Catholique de Louvain, Mycothèque de l'Université catholique de Louvain (MUCL), Croix du Sud 2, Box L7.05.06, 1348 Louvain-la-Neuve, by Symborg, S. L.

*Glomus iranicum* var. tenuihypharum is disclosed in WO2015/000612 and WO2015/000613.

The strain according to the invention, shows a high similarity to *Methylobacterium dankookense* (98.7% based on the sequence of the gen 16S).

A phylogenomic analysis through UBCG showed *Methylobacterium dankookense* as the closest relative to the strain of the invention. Data collected supported the creation of a novel species to accommodate the strain of the invention, for which, for example, the name *Methylobacterium symbioense* nov. could be proposed.

To demonstrate if it could be considered as a new specie, phenotypically and genotypically characterization was assayed.

The strain of the invention is Gram-negative, strictly aerobic, it is in a shape of a bacillus (0.8~1 μm width and 1.2~1.6 μm length) with a lateral flagellum, shown as individually or pairs in two, with no spore forming. The colonies grown on MMM Agar or NFbM Agar for 5 to 7 days are circular, pink colour with a defined clear border, that it has not been described in other similar strains. It has an optimal temperature of 28° C. In the presence of NaCl, the growth rate was reduced till 3% NaCl or higher where it does not grow.

A multigene, genome-based phylogenetic approach was achieved by using UBCG tool in order to better identify the closest relatives to the strain of the invention, CECT 9580. The position of the strain according to the invention was explored in a UBCG tree containing 15 genomes of the relative inside the genus. The tree (FIG. 13) shows a specific relationship to *M. dankookense*.

Advantageously, according to embodiments, the strain according to the invention is characterized by the fact that is an endophyte nitrogen-fixing bacteria able to provide nitrogen to a plant, allowing reduction of external nitrogen input until 60%. In other words, the strain according top the invention allows a reduction of external nitrogen input up to 60%, with respect to the external nitrogen input that it would be necessary in the absence of said strain.

Advantageously, the strain of the invention is able to move through the plant from the roots to the leaves and vice versa.

A process for the isolation of the strain of the invention comprises the following steps:
providing one or more spores of *Glomus iranicum* var. tenuihypharum;
extracting the cytoplasm from the spores;
inoculating the extracted cytoplasm in a methanol-containing medium; and
incubating the inoculated medium to grow the *Methylobacterium* sp. nov. strain of the invention.

According to embodiments, the process for the isolation of the strain of the invention comprises the following steps:
Isolating from spores of *Glomus iranicum* var. tenuihypharum, previously disinfected surfacely through of a process of external disinfection cycles, to obtain spore solution;
after said process, spore solutions are macerated and the fungal cytoplasm is cultivated in a Minimum salt Methanol Medium (MMM);
colonies of the strain of the invention are identified, and one of those, that showed pink colour were picked up and re-isolated from the medium.

According to embodiments, before extracting the cytoplasm, the spores are treated with a disinfectant, to disinfect the outer walls of the spores.

Disinfection of the outer walls of the spores may be carried out according to techniques that are per se known in the art. For example, disinfection of the outer wall of the spores may be carried out by treating the spores with sodium hypochlorite (e.g., a 5% sodium hypochlorite solution in a buffer, for example Tween® 80).

Extraction of the cytoplasm from the spores of *Glomus iranicum* var. tenuihypharum may be carried out according to techniques that are per se known in the art, for example, by macerating the spores in a suitable buffer, preferably Ringer solution's.

After the inoculation of the extracted cytoplasm in a methanol-containing medium (e.g., Minimum salt Methanol Medium (MMM)). Preferably, the methanol-containing medium has the following composition: Methanol, 20.0 ml; $NaNO_3$, 0.5 g; $(NH_4)_2SO_4$, 0.5 g; $MgSO_4.7H_2O$, 0.5 g; $K_2HPO_4$, 1.0 g; $FeSO_4.7H_2O$, 0.01 g; $CaCl_2.2H_2O$, 0.01 g; KCl, 0.5 g; Vitamins Sol., 1.0 ml; Micronutrients Sol., 2.0 ml; Agar, 12 g; pH 7.20. The inoculated medium is incubated, preferably at 28° C. for 5 days, to allow the growing of the *Methylobacterium* sp. nov. strain of the invention.

According to embodiments, the incubation may be carried out at a temperature ranging from 25° C. to 30° C. (preferably at 28° C.).

According to embodiments, the incubation may be carried out at a pH ranging from 5 to 9 (preferably 7).

After the incubation and the growing of the strain of the invention, the colonies are visually identified, by the production of typical pink colour. Then, one or more colonies are picked up and re-isolated, preferably, at least three times to assure that they are clean of any possible contamination.

The strain of the present invention is suitable to be included into a composition.

Another object of the present invention is thus a composition comprising a strain of *Methylobacterium* sp. nov., deposited under accession number CECT 9580.

According to embodiments, the composition of the invention may comprise one or more agriculturally acceptable carrier and/or one or more agriculturally acceptable co-formulants.

Agriculturally acceptable carriers and agriculturally acceptable co-formulants are per se known in the art.

According to embodiments, carriers and/or co-formulants may be selected from the group consisting of talc, clay, maltodextrin, skimmed milk, glucose, vegetable dry extracts, such as those of tea, cassava and quinoa, caolin, coir, Diatomea earth, chitin, $CaCO_3$, alginate, carragens, surfactin, rhamnolipid, sophorolipid, saponin, potassium oleate and mixtures thereof.

According to embodiments, the composition may be in solid form, aqueous liquid form, oily liquid form, emulsion form, semi-solid form or in the form of gel.

Preferably, the composition is in solid form, more preferably, the composition is in powder form.

Also object of the invention is a process for the production of a composition comprising the strain of the invention, i.e., the strain of *Methylobacterium* sp. nov., deposited under accession number CECT 9580.

According to embodiments, the composition of the invention is characterized by the fact that it is applied as seed coating, by soil application, for example, by drip irrigation system or drench, or by foliar application.

The process for producing the composition of the invention comprises the following steps:
Providing at least one *Methylobacterium* sp. nov. deposited under accession number CECT 9580 according to the invention,
Inoculating said *Methylobacterium* sp. nov. in a liquid culture medium including methanol,
Culturing said *Methylobacterium* sp. nov. to obtain a liquid culture comprising *Methylobacteria* and;
Drying said liquid culture to obtain a dry composition.

Advantageously, at the end of the culturing step, the final production of *Methylobacteria* of the invention, is confirmed by measuring of the optical density of the bacteria in the culture and the biomass production.

According to embodiments, *Methylobacterium* sp. nov. deposited under accession number CECT 9580 of the invention is isolated from the inner of the spores of the mycorrhizal fungus *Glomus iranicum* var. tenuihypharum, deposited under BCCM deposit number 54871.

According to embodiments, the medium including methanol is MMMM, i.e., Minimal Mineral Medium with Methanol.

According to embodiments, said step of culturing said *Methylobacterium* sp. nov. to obtain a liquid culture comprising *Methylobacteria* may be carried out by incubation at a temperature ranging from 25° C. to 30° C. (preferably at 28° C.) for 3-10 days, preferably for 5-7 days.

According to embodiments, the above mentioned step of providing at least one *Methylobacterium* sp. nov. of the invention, may comprise a step of recovering the strain of the invention using a nitrogen free medium, for example, NFBG (Nitrogen Free Bacterial Medium supplemented with Glucose) for example NFBG medium may have the following composition: Glucose, Malic acid 5.0 g, Methanol 20.0 ml, $(NH_4)_6Mo_7O_{24}$ $4H_2O$ 0.002 g, $MgSO_4$ $7H_2O$ 0.2 g, $K_2HPO_4$ 0.1 g, $KH_2PO_4$ 0.4 g, $FeCl_3$ 0.01 g, NaCl 0.1 g, KOH 4.8 g, Micronutrients sol. 2.0 ml, Vitamins sol. 1.0 ml, Bromothymol blue sol. 0.5% on KOH 2N 2.0 ml, pH 6.9.

According to embodiments, recovering of the *Methylobacterium* sp. nov. of the invention using a nitrogen free medium may be carried out by incubation at a temperature ranging from 25° C. to 30° C. (preferably at 28° C.) for 3-10 days, preferably for 5-7 days.

Advantageously, the strain of the invention forms colonies of a red-pink color. Thus, colonies of the strain of the invention may be easily identified.

According to embodiments, the above mentioned step of providing at least one *Methylobacterium* sp. nov. of the invention, may further comprise a step of select a colony of the *Methylobacterium* sp. nov. of the invention and selectively grow said *Methylobacterium* sp. nov. using a nitrogen-free, methanol-including medium (e.g., MMMNF, Mineral Minimal Medium with Methanol Nitrogen Free).

According to embodiments, after the selectively grown using a nitrogen-free, methanol-including medium a colony of the *Methylobacterium* sp. nov. of the invention may be selected and inoculated in a liquid culture medium including methanol. According to embodiments, the said step of selectively growing may be carried out by incubation at a temperature ranging from 25° C. to 30° C. (preferably at 28° C.) for 3-10 days, preferably for 5-7 days.

According to embodiments, the above mentioned step of culturing said *Methylobacterium* sp. nov. to obtain a liquid culture comprising *Methylobacteria* may be carried out by fermentation.

According to embodiments, the above mentioned step of culturing said *Methylobacterium* sp. nov. to obtain a liquid culture comprising *Methylobacteria*, may comprise a first step of growing to obtain a culture of *Methylobacterium* sp. nov. to be used as pre-inoculum, and a second step of massive growing, preferably by fermentation.

A further object of the present invention is the use of the strain of *Methylobacterium* sp. nov., deposited under accession number CECT 9580 of the invention as bio-stimulant and/or endophyte nitrogen-fixing bacterium in plants.

In fact, it has been surprisingly observed that the strain of the invention, as well as composition comprising it, is able to stimulate the plant in order to increase the health and the yield of the plant.

Also, advantageously, it has been surprisingly observed that the strain of the invention, as well as composition comprising it, can be used to provide nitrogen to plants. In particular, it has been observed that, by providing the strain of the present invention to a plant, the use of chemical nitrogen fertilizer can be substantially reduced; for example, it has been observed that a reduction in the amount of chemical nitrogen fertilizer of up to 60% may be obtained using the strain of the invention, or a composition comprising it.

Also object of the invention is, thus, the use of *Methylobacterium* sp. nov. strain of the present invention for reducing nitrogen external input, preferably until 60%.

Advantageously, the strain of the invention may be provided to a plant alone, or as a component of a composition including other agriculturally acceptable components.

It has been observed that the strain of the invention can stimulate the plant from the root and/or the aerial part by fixing atmospheric nitrogen. Without being bound to a specific scientific explanation, it has been observed that the strain of the invention penetrates in the tissues of the plant and activates a microbial enzymatic system, comprising a nitrogenase enzyme complex, which reduces the atmospheric nitrogen to $NH_4+$, which might be directly incorporated into Glu (glutamic acid) by amination of 2-oxoglutarate via mitochondrial Glu dehydrogenase (NADH-GDH) and, subsequently, into Glutamine by cytosolic Glutamine synthetase 1 (GS1), under particular physiological conditions. Glutamine oxoglutarate aminotransferase is an enzyme, frequently abbreviated as GOGAT, that produces glutamate from glutamine and α-ketoglutarate and, along with glutamine synthetase, plays a central role in the regulation of nitrogen assimilation in photosynthetic assimilated by the plant.

Advantageously, it has also been observed that the strain of the present invention increases the solubility of phosphorus (which is particularly useful in seedling stages), is able to produce auxins and carotenes, that stimulate the development of secondary roots.

Advantageously, the strain of the invention may be provided to a variety of crops.

For example, the strain of the present invention is particularly useful when provided to horticultural cultivations, gramineous plants, citrus cultivations, cultivation of stone fruits (drupe), vine cultivation and forestry.

Another advantage of the strain of the present invention is that it favors photosynthesis in the host plant, and therefore an increase in plant biomass.

EXPERIMENTAL SECTION

Further aspects and advantages of the present invention will be illustrated with reference to the following non-limiting examples.

The strain of the invention was obtained from *Glomus iranicum* var. tenuihypharum's spores.

It was isolated from the inner of the spores, through a process of several disinfection of the external spore walls by washing them with 0.5% sodium hypochlorite plus Tween 80 for 5 minutes, carrying out 5 disinfection cycles. After it, spore solutions were macerated and sowing the fungal cytoplasm in a Minimum Salt Methanol Medium (MMM) (Methanol, 20.0 ml; $NaNO_3$, 0.5 g; $(NH_4)_2SO_4$, 0.5 g; $MgSO_4.7H_2O$, 0.5 g; $K_2HPO_4$, 1.0 g; $FeSO_4.7H_2O$, 0.01 g; $CaCl_2.2H_2O$, 0.01 g; KCl, 0.5 g; Vitamins Sol., 1.0 ml; Micronutrients Sol., 2.0 ml; Agar, 12 g; pH 7.20) at 28° C. for 5 days. From the medium, 5 different colonies were identified, and the ones that showed pink colour were picked up and re-isolated at least three times to assure that they were clean of any other possible contamination.

Example 1

Trial 1. Routes of Application of the Strain of the Invention.

Experiments have been conducted in cultivation chamber applying the strain of the invention, i.e., *Methylobacterium* sp. nov., strain deposited under accession number CECT 9580, by foliar application, soil application and seed coating, i.e., seed dressing.

The presence of the strain of the invention was assessed in leaves, stems and roots. Travel time of the strain in the plant, from root to leaf and from leaf to root, and penetration of the strain through roots stomata and seed were also evaluated.

In order to corroborate the entry of methylobacteria into the plant and the colonization of different tissues, a trial was carried out, inoculating seeds in alveoli and maize plants in culture pots. In this case three treatments were applied: seed coating, application through irrigation and foliar application. The presence of colonies of the strain of the invention was analyzed in root, stem and leaves of three biological replicas at different hours and days after inoculation ("h.a.i.", and "d.a.i.").

Materials and Methods

Plant Material and Microorganisms Used.

Corn seeds (*Zea mays* L.) coated with Fludioxonil and Mefenoxam fungicides were used as plant material. Bacteria belonging to the strain *Methylobacterium* sp. nov. of the invention and *Herbaspirillum seropedicae* were used as microbial inoculants.

Growing Conditions of Maize Plants.

Figure 1:
FIG. 1 shows plants growing in alveoli in growth chamber.

For the growth of maize plants, small plastic containers were used, with a mixture of sterile substrate based on silica sand and coconut fibre in a ratio of 2:1, arranged in a growth chamber at 24° C. and 60% relative humidity (RH) in the presence of light, as shown in FIG. 1, for 4 weeks. The plants were watered twice a week with sterile decalcified water. After 15 days from sowing, the plants were watered only once with a nutritive solution N:P:K: 4:1.7:4.5 at 0.3%, plus a solution of micronutrients.

Treatments with the Strain of the Invention in Corn Plants.

Different treatments were carried out on corn plants with i.e., the strain of *Methylobacterium* sp. nov. deposited under accession number CECT 9580 by means of seed coating (i.e., seed dressing), by irrigation and by foliar application, i.e., foliar route. The inoculum was used in solid form (powder). The bacterial concentration in the powder was in the order of $1 \times 10^9$ CFU/g. Each treatment studied was compared with plants not treated as negative control. In addition, the nitrogen-fixing bacterium *Herbaspirillum seropedicae* was used as positive control of the trial at a solid format concentration of $1.2 \times 10^6$ CFU/g.

a) Seed Coating.

The corn seeds were coated with *Methylobacterium* sp. nov. strain of the invention powder inoculum.

b) Irrigation Route

After 4 days after sowing, *Methylobacterium* sp. nov. strain of the invention and *Herbaspirillum seropedicae* were inoculated via irrigation with a concentration between $1$-$1.2 \times 10^6$ CFU per plant. For this purpose, the bacterial inoculum in solid form was diluted in water for further treatment.

c) Foliar Route

When the plants presented between two and three true leaves, corresponding with the classification BBCH 12-13, *Methylobacterium* sp. nov. strain of the invention and *Herbaspirillum seropedicae* were inoculated by foliar route. The solid bacterial inoculum was diluted in water to a concentration of $1 \times 10^6$ CFU/plant. Previously, the substrate was covered with plastic to prevent contamination with the treatment. The bacterial treatment was carried out by spraying the leaves with a sprayer.

Detection of *Methylobacterium* sp. Nov. Strain of the Invention Colonies in Root, Stem and Leaf.

Figure 2:
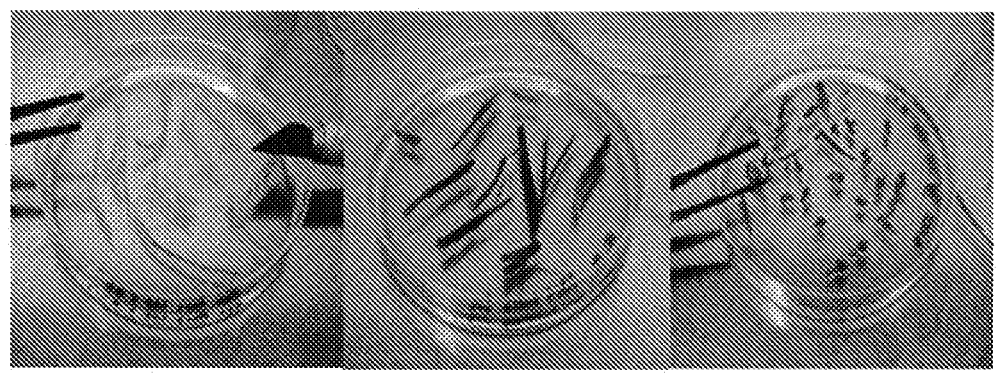
FIG. 2 shows vegetable tissue samples (roots (a), stems (b) and leaves (c)) exposed to specific culture media after disinfection for the growth of methylobacteria.

After treatments with *Methylobacterium* sp. nov. strain of the invention, the presence of this bacterium together with its positive control *Herbaspirillum seropedicae* in different plant tissues was analysed. These were disinfected superficially in order to avoid false positives. To do this, they were immersed for 30 seconds in a solution of ethanol (70%) and sodium hypochlorite (1%) for 2 minutes, with subsequent washing with doubly distilled water. Once disinfected (root and leaf), longitudinal and transverse cuts were made in the stem for subsequent transfer to a specific culture medium for methylobacteria. FIG. 2 shows such plant tissue samples, exposed to specific culture media after disinfection for the growth of methylobacteria. In particular, panel "a" of FIG. 2 shows roots samples, panel "b" of FIG. 2 shows stems samples and panel "c" of FIG. 2 shows leaves samples. Tissue samples placed in culture medium were incubated for 7 days at 28° C. Colony growth was observed in a Leica Wetzlar stereomicroscope, and photos were taken with a MC170 HD Leica camera. The plants were harvested for analysis between 1 and 24 h of the first day and between 2-10 days after inoculation (irrigation and foliar) or germination (coating). Three biological replicas were used for each of the three treatments and times analyzed.

Statistical Analysis of the Results Obtained

For the statistical analysis of the results, the method used was a simple ANOVA together with the Fisher test of minimal significant difference, for a significance level of $p<0.05$. The software STATGRAPHICS Centurion 18 has been used, as well as Microsoft Excel for data processing and graphical representation.

Results

Effect of application of *Methylobacterium* sp. nov. strain of the invention: Infection and colonization of the plant.

(a) Seed Dressing

The first evaluation to detect bacterial colonies in the treated plants inoculated by coating was made at 48 hours, coinciding with the time of germination of the seeds. The analyses revealed that after two days *Methylobacterium* sp. nov. strain of the invention was present in the internal tissue, after 4 days they were in the stem and after 6 days they appeared in the leaves. Therefore, the passage of the bacteria towards the new structures took place as the plant developed.

b) Irrigation

In the case of inoculation via irrigation, the bacteria were in the internal tissues of the root 1 hour and rose to the stem between 4 and 8 days, reaching the leaves 10 after treated. It is good to emphasize that in this case it was not homogeneous in all the replicas.

c) Foliar Route

By foliar route, the bacteria were found in the internal tissue of the leaves 1 hour after inoculation, after 6 hours after treatment, they were detected both in the stem and in the roots.

Figure 3:
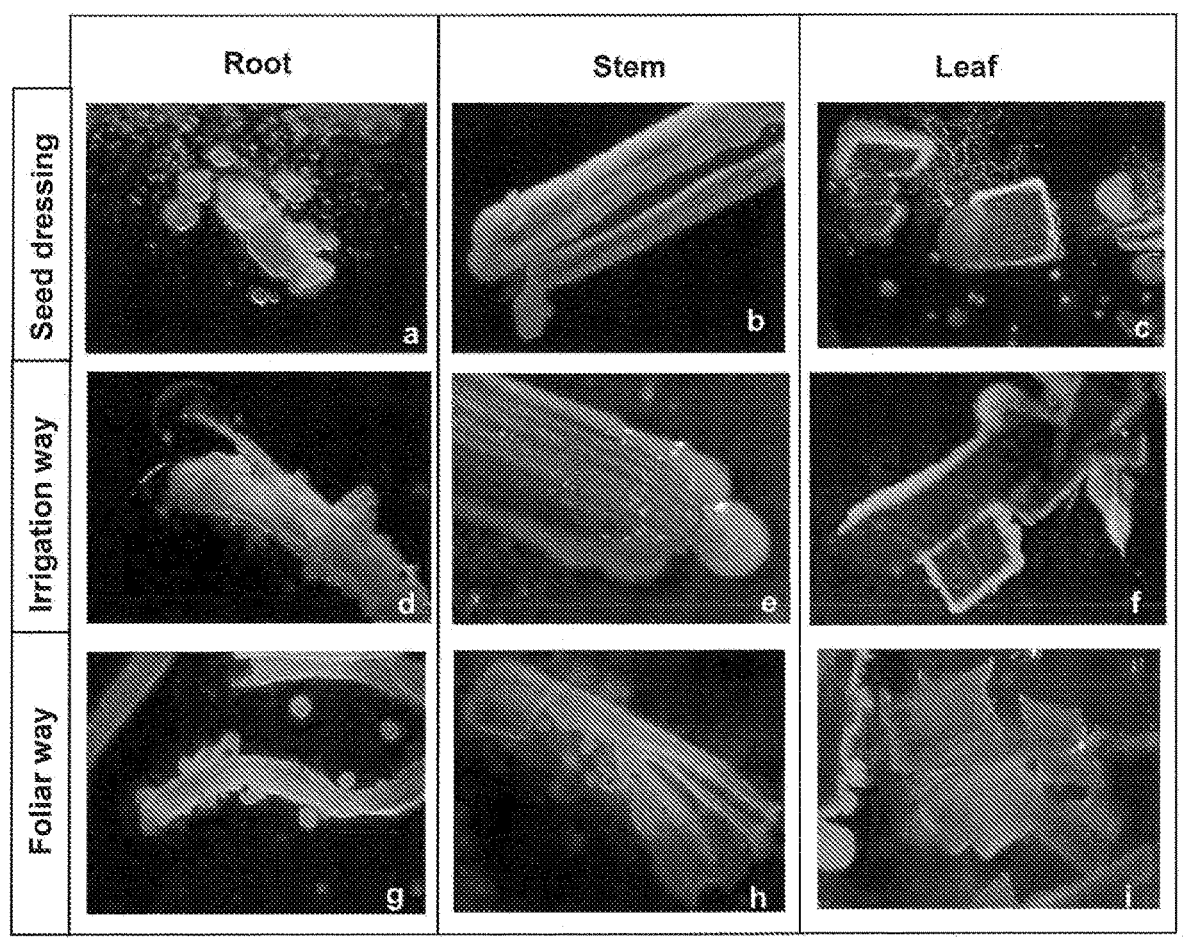
FIG. 3 shows images of plant tissues samples of plants treated with the strain of the invention by seed dressing (a-c), by irrigation (d-f) and foliar application (g-i), exposed to a specific nutrient medium for methylobacteria.

FIG. 3 shows images of the plant tissues samples of plants treated with the strain of the invention by seed dressing (a-c), by irrigation (d-f) and foliar application (g-i), exposed to a specific nutrient medium for methylobacteria.

Table 1, here below reported, shows data related to the detection of colonies of *Methylobacterium* sp. nov. strain of the invention in different parts of the plant for 10 days. Legend: H: hours, d: day, presence of bacteria in 20-40% (+), 50-80% (++) and 90-100% (+++). Stem A: Apical Stem; Stem B: Basal Stem.

TABLE 1

| Treatments | Plant | 1 h | 3 h | 6 h | 9 h | 12 h | 24 h | 2 d | 3 d | 4 d | 6 d | 8 d | 10 d |
|---|---|---|---|---|---|---|---|---|---|---|---|---|---|
| Control | Root | − | − | − | − | − | − | − | − | − | − | − | − |
| | Stem A | − | − | − | − | − | − | − | − | − | − | − | − |
| | Stem B | − | − | − | − | − | − | − | − | − | − | − | − |
| | Leaf | − | − | − | − | − | − | − | − | − | − | − | − |
| Seed treatment | Root | − | − | − | − | − | − | +++ | +++ | +++ | +++ | ++ | ++ |
| | Stem A | − | − | − | − | − | − | − | − | +++ | +++ | ++ | ++ |
| | Stem B | − | − | − | − | − | − | − | − | +++ | +++ | ++ | ++ |
| | Leaf | − | − | − | − | − | − | − | − | − | ++ | + | + |
| Irrigation | Roof | + | ++ | ++ | ++ | ++ | ++ | + | + | + | +++ | +++ | +++ |
| | Stem A | NA | NA | NA | NA | NA | NA | − | − | + | + | + | ++ |
| | Stem B | NA | NA | NA | NA | NA | NA | − | − | − | − | − | ++ |
| | Leaf | NA | NA | NA | NA | NA | NA | − | − | − | − | − | ++ |
| Foliar application. | Root | NA | NA | NA | NA | NA | NA | − | − | − | + | + | ++ |
| | Stem A | NA | NA | NA | NA | NA | NA | − | − | − | + | + | ++ |
| | Stem B | NA | NA | NA | NA | NA | NA | − | − | − | + | + | ++ |
| | Leaf | +++ | +++ | +++ | ++ | ++ | ++ | + | + | + | ++ | ++ | +++ |

Conclusions

In this trial it was determined that the entry of the microorganism was effective both through the root zone and by the aerial part. Therefore, in the plants treated by any method, colonies of *Methylobacterium* sp. nov. strain of the invention were located, which indicates that this endophyte microorganism is transported from the root to the leaf and back.

Example 2 Trial 2. Efficacy of the Use of the Strain of the Invention in the Reduction of 40% of Nitrogen Fertilizer in the Cultivation of Long-Cycle Maize Objectives.

To know the efficacy of the strain of the invention on the development of corn (maize), against the reduction of 40% of nitrogen cover fertilization in conventional growing conditions, through the evolution of the green color of the leaf (SPAD), vegetation indexes, levels of nitrogen in the plant, concentration of the microorganism in leaf and production yield.

Materials and Methods.

Trial Fields and Fertilization.

The trial was carried out in Spain, in three farms in Huesca. The first farm with coordinates 41° 52'12.7"N 0° 23'11.1" Win Montesusin, Huesca; the second farm with coordinates 41° 40'47.6"N 0° 17'09.5" E Belver de cinca, Huesca; the third farm with coordinates 41° 47'58.1"N 0° 23'56.0" E Tamarite de litera, Huesca.

The fertilization recommendations were conventional fertilization and a 40% reduction in nitrogen reduction treatments. For this purpose, fertilizer was distributed with a fertilizer spreader with the quantities specified in Table 2, here below reported.

Table 2 shows quantity, type of fertiliser and nitrogen fertiliser units (NFU) used in each fertiliser on each plot.

TABLE 2

|  | Control | | Treated | |
| --- | --- | --- | --- | --- |
|  | Fund Fertilization | Cover Fertilization | Fund Fertilization | Cover Fertilization |
| Field 1 | 500 kg NPK 6-9-11 + 280 kg NPK 18-46-0 | 700 kg N32 | 500 kg NPK 6-9-11 + 280 kg NPK 18-46-0 | 333 kg N32 |
| Field 2 | 10 ton chicken compost | 652 kg urea N 46 | 10 ton chicken compost | 250 kg urea N46 |
| Field 3 | 35 ton sheep compost + 600 kg D-Coder ® | 650 kg 30N-15S | 35 ton sheep compost + 600 kg D-Coder ® | 334 kg 30N-15S |

|  | Total UFN Control 100% NFU | Total UFN Treated 60% NFU | Common Fertilization Fund (NFU) | Control Cover (NFU) | Treated Cover (NFU) |
| --- | --- | --- | --- | --- | --- |
| Field 1 | 293 | 175 | 59 | 224 | 104 |
| Field 2 | 480 | 295 | 180 | 300 | 115 |
| Field 3 | 237 | 142 | 42 | 195 | 100 |

Distribution of the Treatments in the Fields.

The fields had the following surface: Field 1 (5.43 ha), Field 2 (3.28 ha) and Field 3 (2.34 ha). Two contiguous areas of 16 meters wide were taken for the evaluation of the parameters. The area marked with "1" is the treated area and the area marked with "2" is the control area.

Figure 4:
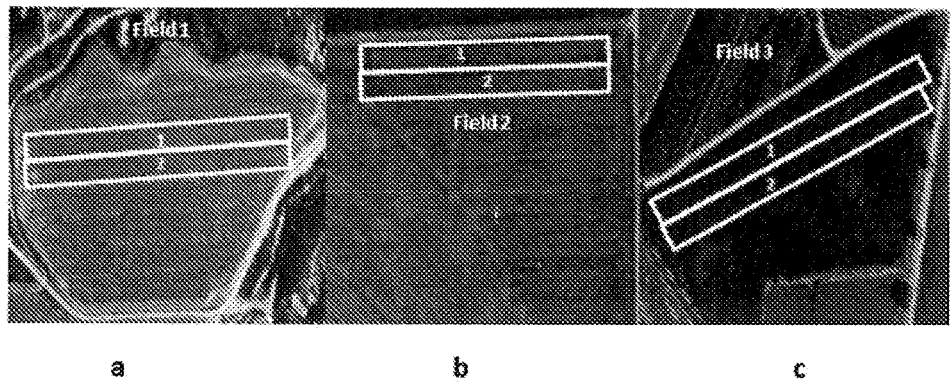
FIG. 4 shows images of the distribution of trials with treatment 1 with the strain of the invention and treatment 2 control. Field 1 (a), Field 2 (b), Field 3 (c).

FIG. 4 shows the distribution of tests with treatment 1 (in area 1) with *Methylobacterium* sp. nov. strain of the invention and treatment 2 control (in area 2).

In particular, panel "a" of FIG. 4 shows Field 1, panel "b" of FIG. 4 shows Field 2 and panel "c" of FIG. 4 shows Field 3.

Characteristics of the Culture and Application of *Methylobacterium* sp. Nov. Strain of the Invention in Corn of Long Cycle.

Corn seeds (*Zea mays*) were selected for grain of the variety "40F" with a plantation ratio of 300 kg/ha, sown at a depth of 3 cm with a separation between rows of 75 cm and separation within the same row of 15 cm. The width of each sowing lane is 16 m between sprinklers. The date of sowing was from 1 to 5 May 2018, after five days the stem emerged and the date of application of *Methylobacterium* sp. nov. strain of the invention was 40 days after sowing, on 12 Jun. 2018 and was sown, using a seed drill in the fields indicated by farmers, representative area of corn cultivation in Spain. A random design was made choosing a plot of the field for each treatment.

The *Methylobacterium* sp. nov. strain of the invention was applied at a dose of 333 g/ha ($3 \times 10^7$ CFU/g) by foliar application, with a 40% reduction in nitrogen fertilization. The results were compared with a conventional fertilization treatment. Foliar application was performed with a sprayer with 300-400 liters of broth per hectare, when the plant was in stage 13-14 of the BBCH scale, with an air temperature of 17° C. and a relative humidity of 52%, with a wind speed of 2.3 mps north direction, without the presence of dew on the leaves and a cloudiness of 60%.

Parameters and Evaluation Methodology

Counting Colony-Forming Units Per Gram of Leaf (CFU/g)

This parameter was measured to be certain that the microorganism is in the whole culture cycle and in what quantity on the leaves. It is measured by taking one gram of leaves from the fourth leaf from below 20 plants and making serial dilutions by sowing them in nitrogen-free selective culture media with methanol as the carbon source.

SPAD (Chlorophyll Level in Leaf)

This parameter is an indicator of the plant's good nutritional status and is closely related to nitrogen and iron levels. For this, a meter known as SPAD (Soil Plant Analysis Development) was used and 100 measurements were made of the fourth leaf from below 100 plants of each treatment.

Nitrogen in Leaf, Stem and Cob Grain

This parameter is an indicator of the amount of nitrogen in each plant tissue accumulated at the time of harvest. The leaf, stem and cob grain are taken from 100 plants to analyse total nitrogen by Kjeldahl's method.

Photos of Dron (Flight of Dron to Obtain Different Indexes)

NDVI (Normalized Difference Vegetation Index). Contrasts the bands of red light and near infrared reflected in the leaves of the plants. It is a general indicator of canopy density and is often used to distinguish living green vegetation from soil that looks blue the more chlorophyll it has.

Combined CIR (Color InfraRed). Infrared composite color that combines NIR (near infrared), Red and Green bands. Healthy vegetation reflects a high level of NIR (near infrared) and looks red. Latent vegetation is often green or bronzed, while sandy soils are light brown and clay soils are dark brown or bluish green.

Yield

In order to evaluate the yield of the harvest, 6 random blocks are taken and 30 square meters of surface area are harvested. The obtained grain is weighed discounting the loss by humidity in each zone.

Statistical Analysis

The factors (SPAD and performance) and their interaction were analyzed for each parameter by ANOVA, using Statgraphics Plus software for Windows 5.1 (Manugistics, Inc., USA).

Results
Counting of Colony Forming Units (CFU)

Table 3, here below reported, shows data related to colony-forming units (CFU) per gram of leaf and in the application tank, after treatment (Apr. 6, 2018) and after one month from treatment (Apr. 6, 2018).

TABLE 3

|  | Jun. 4, 2018 | | Jul. 4, 2018 |
|---|---|---|---|
|  | CFU/ml application Tank | CFU/gr Leaf | CFU/gr Leaf |
| Field 1 | 2.50E+04 | 4.40E+02 | 7.00E+02 |
| Field 2 | 2.50E+04 | 3.30E+03 | 4.20E+03 |
| Field 3 | 2.50E+05 | 8.00E+02 | 1.20E+03 |

In the application tank there was a homogeneous mixture of the product and a correct application in the plant that, after one month of application in corn leaf the populations are maintained and increase their growth as can be seen in all the plots.

SPAD

Figure 5:
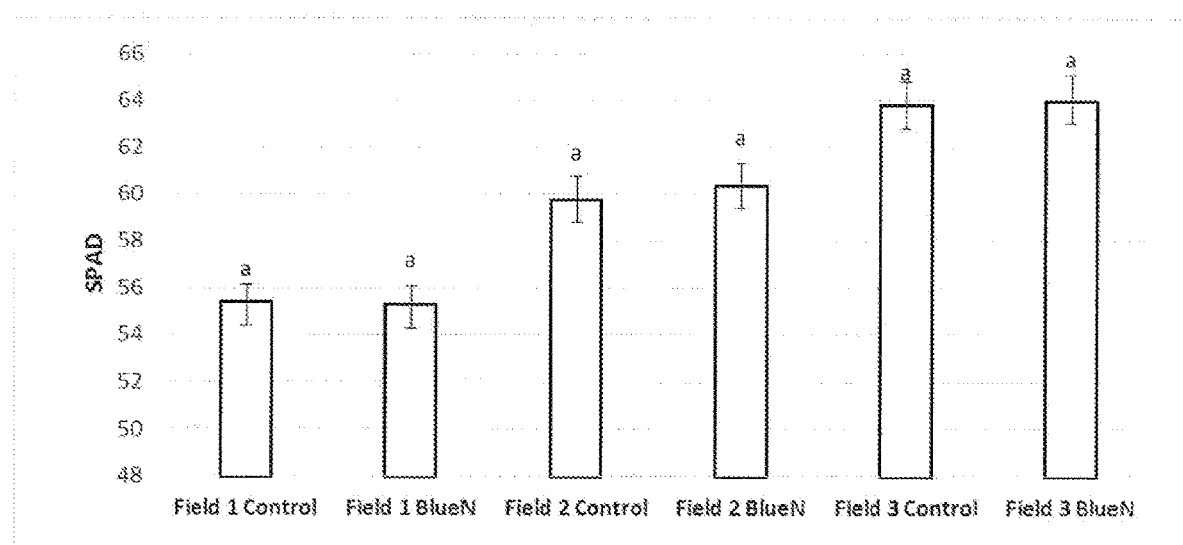
FIG. 5 shows a graph with SPAD measurements after 30 days of application.

FIG. 5 shows SPAD measurement 30 days after application of *Methylobacterium* sp. nov. strain of the invention.

After one month from the application plants maintained SPAD levels equal to the control, without significant differences in all the fields, verifying that the reduction of chemical nitrogen has not had a negative effect on the plant since it has been contributed by the bacteria.

Nitrogen in Leaf, Stem and Cob

Table 4, here below reported, shows data concerning, nitrogen concentrations (g/plant) found in the different tissues of the maize plant at the time of harvest.

TABLE 4

|  | Field 1 | | Field 2 | | Field 3 | |
|---|---|---|---|---|---|---|
|  | Control | Treated | Control | Treated | Control | Treated |
| Leave | 0.39 | 0.37 | 0.58 | 0.37 | 0.35 | 0.36 |
| Stem | 0.71 | 0.76 | 1.80 | 0.51 | 0.72 | 0.76 |
| Grain | 1.63 | 2.08 | 1.81 | 3.16 | 1.70 | 1.71 |
| Total | 2.73 | 3.22 | 4.19 | 4.05 | 2.76 | 2.84 |

Drone Photos (45 dat)

Figure 6:
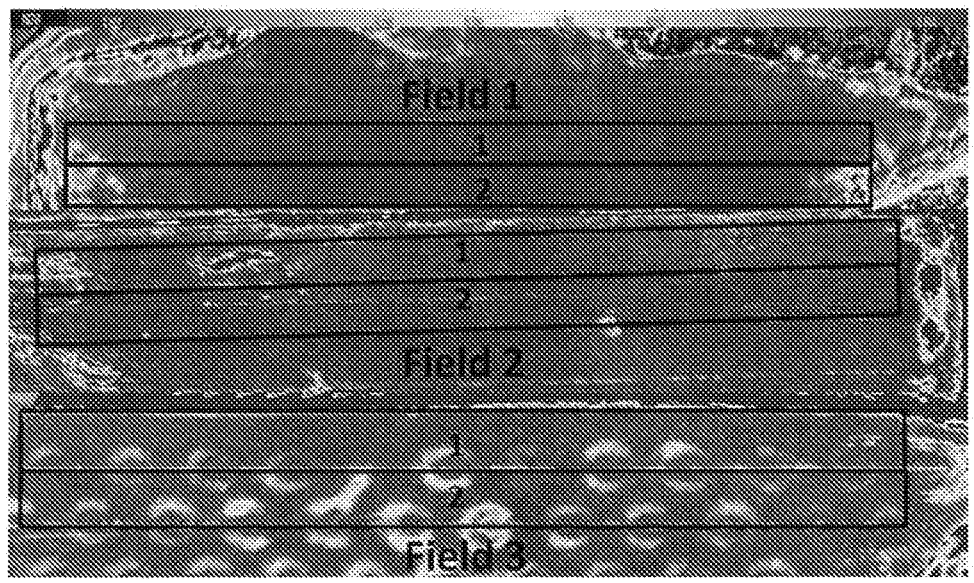
FIG. 6 shows NDVI index for field 1 (a), field 2 (b) and field 3 (c).

FIG. 6 shows drone photos used for NDVI index determination, for field 1 (panel "a"), field 2 (panel "b") and field 3 (panel "c").

Figure 7:
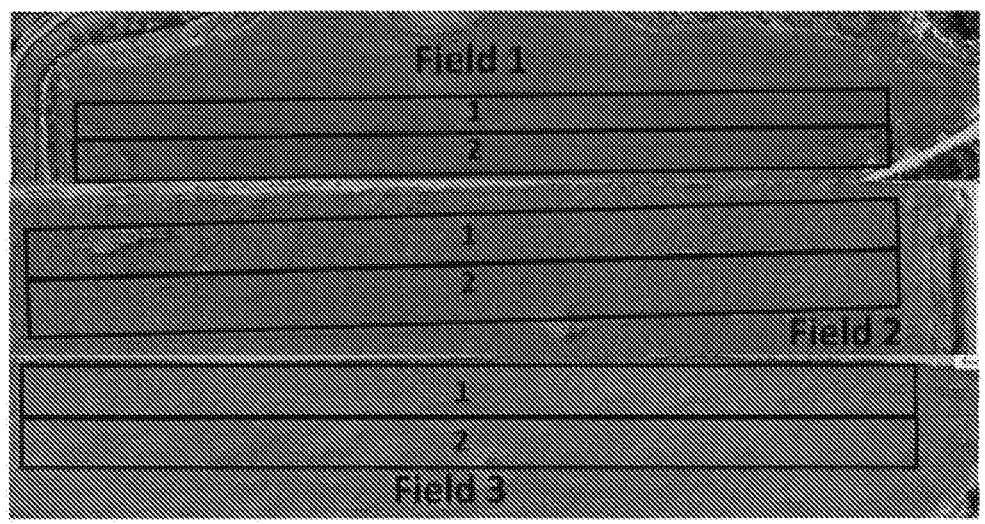
FIG. 7 shows combined CIR index for field 1(a), field 2 (b) and field 3 (c).

FIG. 7 shows drone photos used for combined CIR index determination, for field 1 (panel "a"), field 2 (panel "b") and field 3 (panel "c").

Considering indexes NDVI and combined CIR, no differences were observed in the density of the plant canopy, chlorophyll and plant health (intensity of blue and red color) in any of the fields, compared to the control, except in field, 3 where there was a problem with the irrigation water pressure and a color difference is observed in the crop in the areas where the sprinkler did not water properly.

Yield

Table 5, here below reported, shows data concerning the yield of each field.

TABLE 5

|  | Yield (kg/ha) | | Increase % (kg/ha) |
|---|---|---|---|
|  | control | Treated | treated |
| Field 1 | 16881 a | 17511 b | 3.96 |
| Field 2 | 14346 a | 18335 b | 27.8 |
| Field 3 | 14312 a | 17539 b | 22.5 |

In Table 5, the averages followed by different letters on the line differ significantly from each other.

In field 1, the control had a yield of 16881 kg/ha. With the application of the *Methylobacterium* sp. nov. strain of the invention, a yield of 17511 kg/ha was obtained; which meant 4% more production.

In field 2 the control had a yield of 14346 kg/ha. The application of the *Methylobacterium* sp. nov. strain of the invention produced a yield of 18335 kg/ha, i.e., a productive increase of 28%.

In field 3, the control yielded 14312 kg/ha. The application of the *Methylobacterium* sp. nov. strain of the invention generated a yield of 17539 kg/ha, resulting an increase in net production of 22.5%

Table 6, here below reported, shows data concerning Nitrogen balance—nitrogen provided (input) via fertilization, nitrogen assimilated by the plant after extraction, balance of assimilation between the input and extracted in the plant. Nitrogen requirement (i.e., input required) per ton of grain and nitrogen extraction per ton of grain.

TABLE 6

|  | Input UFN/ha | Extraction of plant (Kg N/ha) | Balance of assimilation (UFN/ha) (Extraction − Input) | Input required (UFN/ ton grain) | Extraction (kg N/ ton grain) |
|---|---|---|---|---|---|
| Field 1 Treated | 175 | 286.63 | 111.63 | 9.99 | 16.36 |
| Field 1 Control | 293 | 243.40 | −49.59 | 17.35 | 14.41 |
| Field 2 Treated | 295 | 361.00 | 66.00 | 16.08 | 20.61 |
| Field 2 Control | 480 | 373.38 | −106.61 | 33.45 | 22.11 |
| Field 3 Treated | 142 | 246.23 | 104.22 | 8.09 | 14.06 |
| Field 3 Control | 237 | 253.45 | 16.44 | 16.55 | 15.01 |

Conclusions

*Methylobacterium* sp. nov. strain of the invention has an efficient application in the cultivation of corn and persistence of the microorganism in the plant.

The strain of the invention maintains a level of SPAD (chlorophyll), plant health and plant canopy density (NDVI index and combined CIR index) equal to the conventional fertilization, wherein a higher amount of nitrogen fertilizer is used.

The strain of the invention provides 40% of the total nitrogenous fertilizer units that were reduced in the fertilization of cover and also provides an increase in the production of between 4 and 27%. As the plants only had one cob per plant, this increase would be linked to the specific weight of the grain and/or number of runs.

If we observe the balance of the nitrogenous fertilizer units contributed via fertilization and the extraction of the nitrogen in the plant that was carried out, there is a nitrogen gain of between 66 and 111 kg of nitrogen per hectare. This means that those kilograms of nitrogen were fixed by the strain of the invention during the culture cycle. This result is indirectly observed in the nitrogen requirement per ton of grain produced in the treated plants, since the requirement to produce one ton of grain is less than the controls. It must also be borne in mind that the requirements to produce a ton of treated grain are lower than the extraction of nitrogen that was made to produce that ton of grain. It is the opposite in the control, since more nitrogen is needed to produce the same amount of grain.

Example 3

Trial 3. Efficacy of the Use of *Methylobacterium* sp. Nov. Strain of the Invention in the Reduction of 30% of the Nitrogen Fertilizer in the Short Cycle Cultivation of Maize.
Objectives.

To know the effectiveness of *Methylobacterium* sp. nov. strain of the invention on the development of corn (maize), against the reduction of 30% of nitrogen cover fertilization under conventional growing conditions through the evolution of green color of the leaf (SPAD), vegetation indexes, nitrogen levels in the plant, concentration of the microorganism in the leaf and the productive yield.

Materials and Methods

Trial Fields and Fertilization.

The trial was carried out in Spain, in two fields: a field of Pomar de Cinca in Huesca with coordinates 41° 50'13.8 "N 0° 05'38.0" E and the other in Finca Oran, Albacete with coordinates 38° 49'55.3" N 1° 50'27.1" W.

Fertilization recommendations were conventional fertilization and a 30% reduction in nitrogen reduction treatments. For this, fertilizer was distributed with a fertilizer spreader with the quantities specified in table 7, here below reported.

Table 7 shows quantity, type of fertiliser and nitrogen fertiliser units (NFU) used in each fertiliser on each plot.

TABLE 7

| | Control | | Treated | |
|---|---|---|---|---|
| | Fund Fertilization | Cover fertilization | Fund fertilization | cover fertilization |
| Field 1 | 250 kg Urea 46 | 250 kg Urea 46 | 150 kg Urea 46 | 100 kg Urea 46 |
| Field 2 | 700 kg NPK 8-14-14 | 550 kg N 40-0-0 | 700 kg NPK 8-14-14 | 330 kg N 40-0-0 |

| | Control 100% NFU | Treated 60% NFU | Common Fertilization Fund (NFU) | Control Cover(NFU) | Treated Cover(NFU) |
|---|---|---|---|---|---|
| Field 1 | 230 | 161 | 115 | 115 | 46 |
| Field 2 | 276 | 188 | 56 | 220 | 132 |

Distribution of the Treatments in the Fields

The fields had the following surface: Field 1 (74 ha), Field 2 (3.67 ha) and two contiguous areas of 16 meters wide were taken for the evaluation of the parameters. The area marked with "1" is the treated area and the area marked with "2" is the control area.

Figure 8:
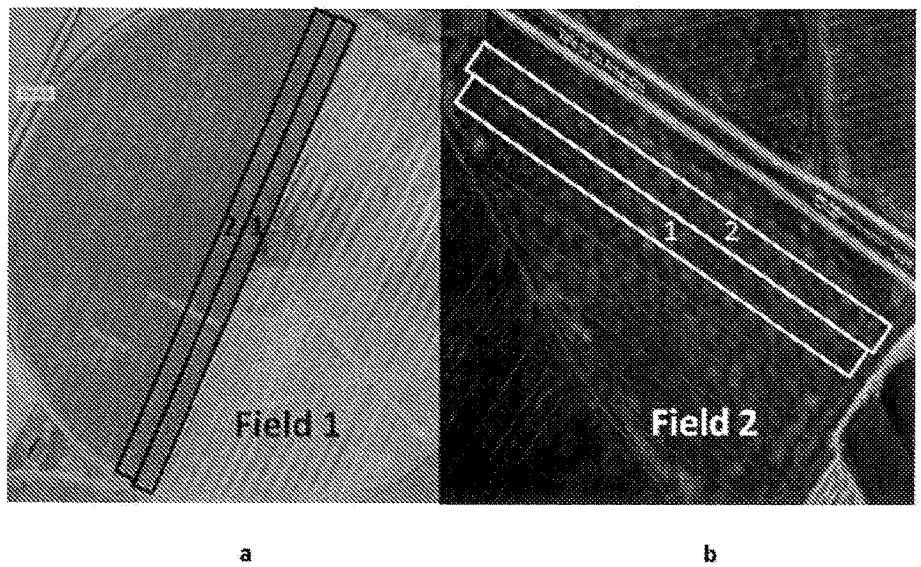
FIG. 8 shows images of the distribution of trials with treatment 1 with the strain of the invention and treatment 2 control. Field 1 (a), Field 2 (b).

FIG. 8 shows the distribution of tests with treatment 1 (in area 1) with *Methylobacterium* sp. nov. strain of the invention and treatment 2 control (in area 2). In particular, panel "a" of FIG. 8 shows Field 1 and panel "b" of FIG. 8 shows Field 2.

Characteristics of the Culture and Application of the *Methylobacterium* sp. Nov. Strain of the Invention Corn seeds of the variety "Guasi" were selected in field 1 and variety DKC 5032 YG in field 2, with a planting ratio of 300 kg/ha, sown to a depth of 3 cm with a separation between rows of 75 cm and separation within the same row of 15 cm. The width of each sowing lane is 16 m. The sowing date was 20 June on field 1 and 30 June on field 2, after ten days the stem emerged and the date of application of *Methylobacterium* sp. nov. strain of the invention was 22 and 20 days respectively after sowing, 12 July (Field 1) and 20 Jul. 2018 (Field 2). *Methylobacterium* sp. nov. strain of the invention was applied at a dose of 333 g/ha ($3\times10^7$ CFU/g) by foliar application.

Foliar application was performed with a sprayer machine with 300-400 liters of broth per hectare, when the plant was in stage 13-14 of the BBCH scale, with an air temperature of 22 and 20° C. and a relative humidity of 72 and 58%, with a wind speed of 2.3 and 12 mps north and northwest direction, without the presence of dew on the leaves and a cloudiness of 0 and 15% respectively.

Parameters and Evaluation Methodology
Counting Colony-Forming Units Per Gram of Leaf (CFU/q)

This parameter was measured to be certain that the microorganism is in the whole culture cycle and in what quantity on the leaves. It is measured by taking one gram of leaves from the fourth leaf from below 20 plants and making serial dilutions by sowing them in nitrogen-free selective culture media with methanol as the carbon source.

SPAD (Chlorophyll Level in Leaf)

This parameter is an indicator of the plant's good nutritional status and is closely related to nitrogen and iron levels. For this, a meter known as SPAD (Soil Plant Analysis Development) was used and 100 measurements were made of the fourth leaf from below 100 plants of each treatment.

Nitrogen in Leaf, Stem and Cob Grain

This parameter is an indicator of the amount of nitrogen in each plant tissue accumulated at the time of harvest. The leaf, stem and cob grain are taken from 100 plants to analyse total nitrogen by Kjeldahl's method.

Satellite Photos

The photos from the ESA Copernicus satellite are downloaded and processed with the Qgis program to obtain the NDVI index.

NDVI (Normalized Difference Vegetation Index). It contrasts the bands of red light and near infrared reflected in the leaves of the plants. It is a general indicator of canopy density and is often used to distinguish living green vegetation from soil that looks blue the more chlorophyll it has.

Yield

In order to evaluate the yield of the harvest, 6 random blocks are taken and 30 square meters of surface area are harvested. The obtained grain is weighed discounting the loss by humidity in each zone.

Statistical Analysis

The factors (SPAD and yield) and their interaction were analyzed for each parameter by ANOVA, using Statgraphics Plus software for Windows 5.1 (Manugistics, Inc., USA).

Results
Counting of Colony Forming Units (CFU)

Table 8, here below reported, shows data related to colony-forming units (CFU) per gram of leaf in and the application tank (12-20 Jul. 2018), after treatment (12-20 Jul. 2018) and after one month from treatment (15 Aug. 2018).

TABLE 8

|  | Jul. 12-20, 2018 | | Aug. 15, 2018 |
|---|---|---|---|
|  | CFU/ml Application tank | CFU/gr leaf | CFU/gr Hoja |
| Field 1 | 2.70E+02 | 5.40E+03 | 1.00E+04 |
| Field 2 2 | 1.20E+03 | 3.00E+03 | 8.10E+03 |

In the application tank there was a homogeneous mixture of the product and a correct application in the plant that, after one month of application in corn leaf, the populations are maintained and increase their growth as can be seen in all the fields.

SPAD

Figure 9:
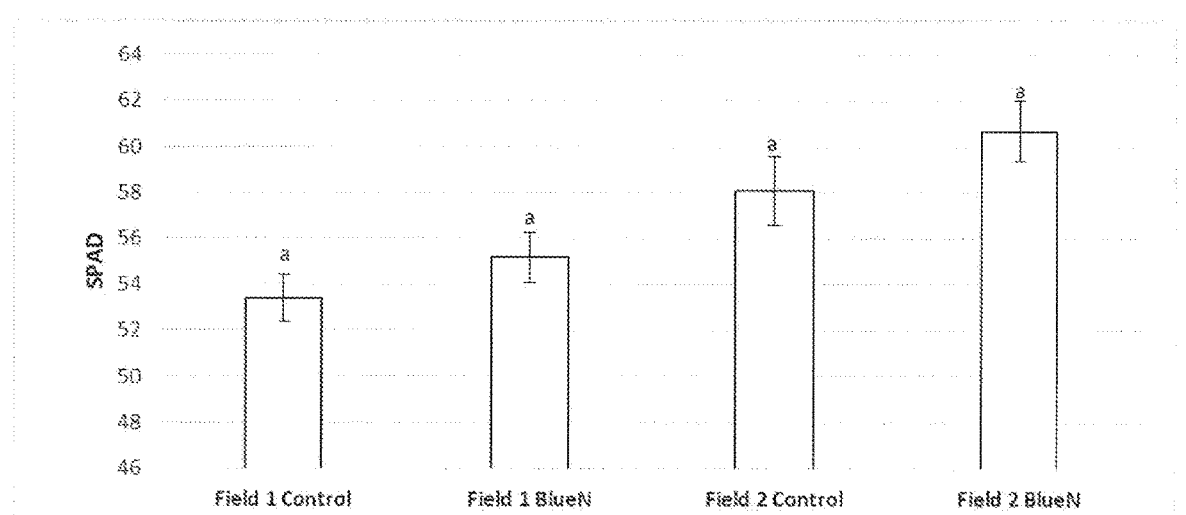
FIG. 9 shows a graph with SPAD measurements after 30 days of application.

FIG. 9 shows SPAD measurements 30 days after application.

After one month from the application plants maintained SPAD levels equal to the control, without significant differences in all the fields, verifying that the reduction of chemical nitrogen has not had a negative effect on the plant since it has been contributed by the bacteria.

Nitrogen in Leaf, Stem and Cob

Table 9, here below reported, shows data concerning amount of nitrogen (grams) of each tissue of the corn plant.

TABLE 9

|  | Field 1 | | Field 2 | |
|---|---|---|---|---|
|  | Control | Treated | Control | Treated |
| Leaf | 0.35 | 0.49 | 0.49 | 0.58 |
| Stem | 0.46 | 0.58 | 0.58 | 0.86 |
| Grain | 1.09 | 1.38 | 1.30 | 1.14 |
| Total | 1.90 | 2.45 | 2.37 | 2.58 |

Satellite Photos.

Figure 10:
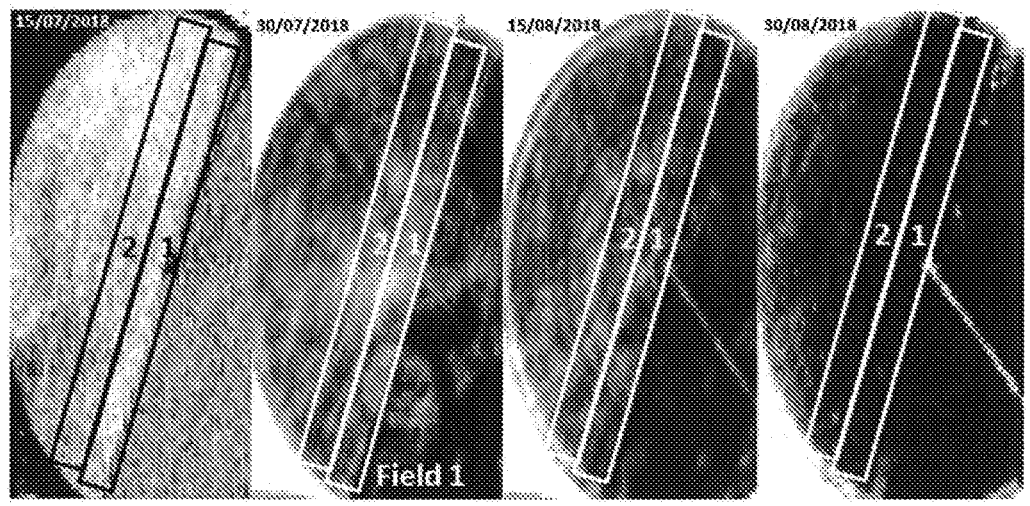
FIG. 10 shows index NDVI in Field 1 after 45 days of treatment, measured every 15 days.
Figure 11:
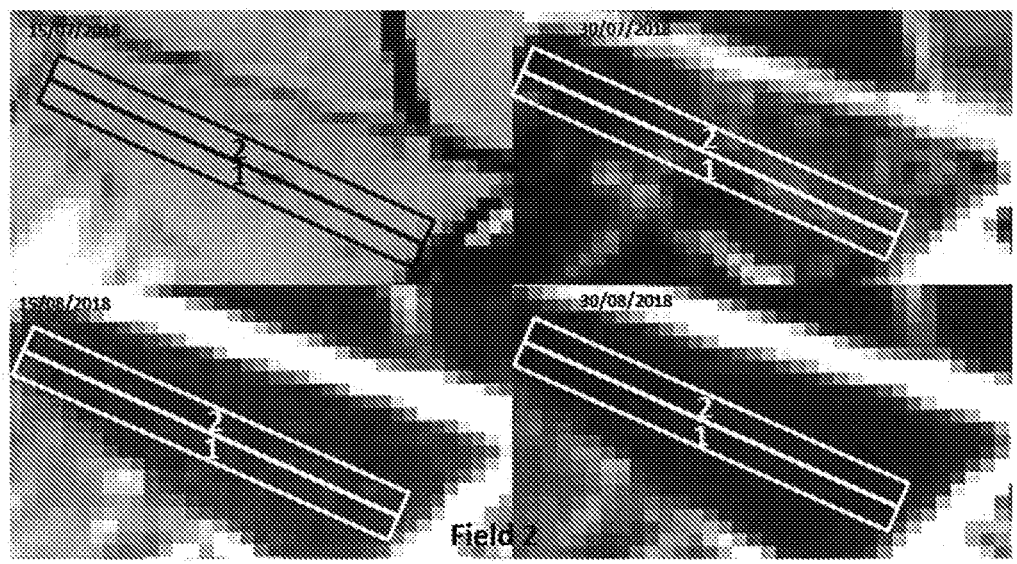
FIG. 11 shows index NDVI in Field 2 after 45 days of treatment, measured every 15 days.

FIG. 10 shows satellite photos used for NDVI index determination for field 1 after 45 days of the treatment measured every 15 days FIG. 11 shows satellite photos used for NDVI index determination for field 2 after 45 days of the treatment measured every 15 days.

A homogeneity in the value of NDVI (intensity of green color) is observed throughout the cultivation cycle comparing the control, with the treatment with the *Methylobacterium* sp. nov. strain of the invention with reduction of fertilization.

Yield

Table 10, here below reported, shows data concerning the yield of each field

TABLE 10

|  | Yield (kg/ha) | | Increase % (kg/ha) |
|---|---|---|---|
|  | Control | Treated | Treated |
| Field 1 | 10515 a | 11828 b | 12.48 |
| Field 2 | 12525 a | 12863 b | 2.7 |

In Field 1 the control had a yield of 10515 kg/ha, however with the application of the strain of the invention a yield of 11828 kg/ha was obtained, with a productive increase of 12.5%.

In field 2 the control had a yield of 12525 kg/ha, and with the strain of the invention a yield of 12863 kg/ha was obtained, for an increase of 2.7%.

Table 11 shows data concerning nitrogen balance: nitrogen provided via fertilization, nitrogen assimilated by the plant after extractions, balance of assimilation between the input and extracted in the plant. Nitrogen requirement per ton of grain and nitrogen extraction per ton of grain.

TABLE 11

|  | Input UFN/ha | Extraction of plants (Kg N/ha) | Balance of assimilation (UFN/ha) (Extraction-input) | Input required (UFN/ ton grain) | Extraction kg N/ ton grain |
|---|---|---|---|---|---|
| Field 1 Treated | 161 | 216.46 | 57.46 | 13.61 | 18.47 |
| Field 1 Control | 230 | 170.03 | −59.97 | 21.87 | 10.95 |
| Field 2 Treated | 188 | 361.00 | 43.30 | 14.61 | 17.98 |
| Field 2 Control | 276 | 373.38 | −65.08 | 22.03 | 16.83 |

Conclusions

*Methylobacterium* sp. nov. strain of the invention has an efficient application in the cultivation of corn and persistence of the microorganism in the plant.

*Methylobacterium* sp. nov. strain of the invention maintains a level of SPAD (chlorophyll), plant health and plant canopy density (NDVI Index) equal to the conventional fertilization, wherein a higher amount of nitrogen fertilizer is used.

With respect to the yield, the strain of the invention provides 30% of the total nitrogenous fertilizer units that were reduced in the cover fertilization and also provides an increase in the production of between 2.7 and 12.5%. As the plants only had one cob per plant, this increase would be linked to the specific weight of the grain and/or number of runs.

If we observe the balance of the nitrogenous fertilizer units provided via fertilization and the extraction of nitrogen in the plant that was carried out, there is a nitrogen gain of between 43 and 57 kg of nitrogen per hectare. This means that those kilograms of nitrogen were fixed by the strain of the invention during the growing cycle. This result is indirectly observed in the nitrogen requirement per ton of grain produced in the plants treated with the strain of the invention, since the requirement to produce one ton of grain is lower than the controls. It must also be taken into account that the requirements to produce one ton of treated grain are lower than the extraction of nitrogen that was made to produce that ton of grain and in the control it is the opposite, since more nitrogen is needed to produce the same amount of grain.

Example 4

Trial 4—Evaluation of *Methylobacterium* sp. Nov. Strain of the Invention in Strawberry Culture for Different Doses of Nitrogen Fertilization Objectives.

To know the efficacy of *Methylobacterium* sp. nov. strain of the invention on the development of the strawberry crop subjected to different doses of nitrogen fertilization of 0, 25, 50, 75 and 100% of the conventional fertilization, through the evolution of the green color of the leaf (SPAD), nitrogen levels in the plant, concentration of the microorganism in the leaf and the productive yield.

Materials and Methods

Trial Field and Fertilization.

The trial was carried out in a field located in the experimental farm of Symborg with coordinates 37° 48'59.6"N 1° 05'43.6" W in Los Martinez del Puerto, Murcia. The field consists of 192 m², and was 8 m wide and 24 m long.

The management of irrigation and fertilization is different for all treatments. The mineral fertilization program consists of 5 solutions with different nitrogen content.

Table 12 shows the different fertilizations of the treatments, measured in UFN.

TABLE 12

|  | UFN |
| --- | --- |
| 100% nitrogen fertilization | 670 |
| 75% nitrogen fertilization | 502.5 |
| 50% nitrogen fertilization | 335 |

TABLE 12-continued

|  | UFN |
| --- | --- |
| 25% nitrogen fertilization | 167.5 |
| 0% nitrogen fertilization | 0 |

Treatments

Table 13 refers to 10 treatments based on 5 levels of fertilization that in turn are divided into treated with *Methylobacterium* strain of the invention and untreated.

TABLE 13

| T1. | 0% nitrogen fertilization |
| --- | --- |
| T2. | 25% nitrogen fertilization |
| T3. | 50% nitrogen fertilization |
| T4. | 75% nitrogen fertilization |
| T5. | 100% nitrogen fertilization |
| T6. | 0% nitrogen fertilization *Methylobacterium* sp. nov. strain of the invention |
| T7. | 25% nitrogen fertilization *Methylobacterium* sp. nov. strain of the invention |
| T8. | 50% nitrogen fertilization *Methylobacterium* sp. nov. strain of the invention |
| T9. | 75% nitrogen fertilization *Methylobacterium* sp. nov. strain of the invention |
| T10. | 100% nitrogen fertilization *Methylobacterium* sp. nov. strain of the invention |

Characteristics of the Culture and Application of *Methylobacterium* sp. Nov. Strain of the Invention Vegetal Material.

Strawberry plants with bare root, variety Fortuna, were planted provided by nurseries.

Frame and Density of Plantation.

The planting frame is 2 m between cultivation rows, 0.1 m between plants, planted in coconut fiber sacks of 1 m×0.18 m×0.15 m in quincunx, giving a density of 100,000 plants per hectare, 10 plants per m², the field consists of 192 m² so that there are 1920 plants for the entire trial.

Date of Planting and Removal of the Crop.

The transplant of the strawberry was made on Feb. 11, 2017, producing the removal of the crop on Jan. 6, 2018.

Hydraulic Design

A 3.5 kv electric pump, that goes to a secondary pipe of 32 mm, that connects with 16 mm hoses with self-compensating external dripper of 3 l/h was used.

Irrigation Water

The irrigation water used in carrying out the trial comes from desalination plant and in the whole trial, 130 liters of water per plant were applied, with a concentration of 0.1 grams per liter of nitrate (13 grams per plant). The characteristics of said water are summarized in the following table (Table 14). Table 14, here below reported, shows data concerning the characteristics of the irrigation water.

TABLE 14

| Parameters | Results |
| --- | --- |
| pH | 7.86 |
| EC (dSm-1) | 0.96 |
| Total dissolved solids (g/l) | 0.507 |
| Chlorine anions (g/l) | 0.245 |
| Sulfate anions (g/l) | 0.0157 |
| Hydroxide anions (g/l) | 0.0001 |
| Carbonate anions (g/l) | 0.074 |
| Nitrate anions (g/l) | 0.101 |
| Soluble phosphorous anions (g/l) | 0.0005 |
| Calcium cations (g/l) | 0.0202 |
| Magnesium cations (g/l) | 0.0084 |

TABLE 14-continued

| Parameters | Results |
| --- | --- |
| Sodium cations (g/l) | 0.134 |
| Potassium cations (g/l) | 0.01 |
| Ammonium cations (g/l) | 0.00077 |
| Boron micronutrients (g/l) | 0.99 |
| Iron micronutrients (g/l) | 0.05 |
| Manganese micronutrients (g/l) | 0.01 |
| Copper micronutrients (g/l) | 0.01 |
| Zinc micronutrients (g/l) | 0.01 |

The strain of the invention was applied at the dose 333 g/ha ($3 \times 10^7$ CFU/g) by foliar application.

The foliar application was carried out with a spray backpack at a rate of 200 liters of broth per hectare when the plant was in stage 13-14 of the BBCH scale, with an air temperature of 20° C. and a relative humidity of 50%, without presence of dew on the leaves, and a cloudiness of 15%.

Parameters and Evaluation Methodology
Counting Colony-Forming Units Per Gram of Leaf (CFU/g)

This parameter was measured to be certain that the microorganism is in the whole culture cycle and in what quantity on the leaves. It is measured by taking one gram of leaves from 50 plants and making serial dilutions by sowing them in nitrogen-free selective culture media with methanol as the carbon source.

Nitrogen in Leaf.

This parameter is an indicator of the amount of nitrogen in each plant tissue accumulated at the time of analysis. 100 plants are taken from the leaf, stem and fruit to analyze total nitrogen by Kjeldahl's method.

Yield

To evaluate crop yield, 30 plants are randomly selected from each treatment and harvested throughout the crop cycle.

Statistical Analysis.

The factor (yield) and their interaction were analyzed for each parameter by ANOVA, using Statgraphics Plus software for Windows 5.1 (Manugistics, Inc., USA).

Results

Counting Colony-Forming Units Per Gram of Leaf (CFU/g)

Table 15, here below reported, shows results concerning Colony forming units per gram of leaf measured monthly from the application.

TABLE 15

| Treatment/ Sampling date | Jan. 18, 2018 | Feb. 15, 2018 | Mar. 15, 2018 | Apr. 15, 2018 |
| --- | --- | --- | --- | --- |
| T 6 | 9.00E+03 | 2.00E+03 | 2.00E+03 | 2.50E+03 |
| T 7 | 2.00E+03 | 1.00E+03 | 8.00E+03 | 8.00E+03 |
| T 8 | 2.00E+03 | 1.00E+03 | 6.40E+03 | 5.00E+03 |
| T 9 | 1.80E+04 | 3.00E+03 | 1.00E+03 | 3.00E+03 |
| T 10 | 2.60E+03 | 1.00E+03 | 1.00E+03 | 1.00E+03 |

By means of colony sampling, a permanence of *Methylobacterium* sp. nov. strain of the invention is observed throughout the culture cycle in the plant.

Total Nitrogen

Table 16, here below reported, shows data related to concentration of Nitrogen (g/100 g of plant), Total Nitrogen (g/plant) and Fresh weight of plants in the strawberry crop.

TABLE 16

| Treatmens | Nitrogen (grams/100 grams of plant) | Average plant weight(grams) | Total Nitrogen (grams/plant) |
| --- | --- | --- | --- |
| T 1 | 1.86 | 7.5 | 0.14 |
| T 2 | 2.52 | 41.4 | 1.04 |
| T 3 | 3.20 | 92.1 | 2.94 |
| T 4 | 3.23 | 96.6 | 3.12 |
| T 5 | 3.31 | 94.7 | 3.13 |
| T 6 | 1.69 | 8.4 | 0.14 |
| T 7 | 2.87 | 65.5 | 1.87 |
| T 8 | 3.24 | 90.1 | 2.91 |
| T 9 | 3.28 | 98.8 | 3.24 |
| T 10 | 3.24 | 90.2 | 2.92 |

Table 16 shows that there is an increase in nitrogen concentration as nitrogen fertilization increases, in both control and those treated with *Methylobacterium* sp. nov. strain of the invention.

An increase of total nitrogen is observed until reaching 75% of nitrogen fertilizer in the plants treated with the strain of the invention, the highest value being found in 3.28, the highest value of nitrogen concentration in plants treated with the strain of the invention. With 100% of the fertilization the N content in the treated plant is reduced.

Production

From the moment they start producing, 30 plants are harvested weekly, randomly selected from each treatment during the entire culture cycle.

Table 17, here below reported, shows the yield in kilograms per plant for each treatment.

TABLE 17

| Treatments | Production (Kg/plant) |
| --- | --- |
| T 1 | 0.24 a |
| T 2 | 0.8 b |
| T 3 | 1.07 c |
| T 4 | 1.05 c |
| T 5 | 1.15 c |
| T 6 | 0.17 a |
| T 7 | 1.04 c |
| T 8 | 1.12 c |
| T 9 | 1.4 d |
| T 10 | 1.02 c |

The treatment with the highest production was 9 (75% of nitrogen with the application of *Methylobacterium* sp. nov. strain of the invention) with 1.4 kilos per plant, significantly different from the other treatments.

Treatments with 0 UFN were those with the lowest production of strawberry kg per plant, with significant differences.

Table 18, here below reported, shows data concerning nitrogen balance: nitrogen provided via fertilization, nitrogen assimilated by the plant after extraction, balance of assimilation between the input (i.e., nitrogen provided) and extracted in the plant.

TABLE 18

| Treatments | Input UFN/ha (irrigation water input 13 UFN) | Extraction of plant (kg N/ha) | Balance of assimilation (UFN/ha) (Extraction-input) |
| --- | --- | --- | --- |
| T 1 | 0 + 13 | 13.95 | 0.95 |
| T 2 | 167.5 + 13 | 104.3 | −76.2 |
| T 3 | 335 + 13 | 294.72 | −53.28 |

TABLE 18-continued

| Treatments | Input UFN/ha (irrigation water input 13 UFN) | Extraction of plant (kg N/ha) | Balance of assimilation (UFN/ha) (Extraction-input) |
|---|---|---|---|
| T 4 | 502.5 + 13 | 312.01 | −203.49 |
| T 5 | 670 + 13 | 313.45 | −369.55 |
| T 6 | 0 + 13 | 14.19 | 1.19 |
| T 7 | 167.5 + 13 | 187.96 | 7.48 |
| T 8 | 335 + 13 | 291.92 | −56.08 |
| T 9 | 502.5 + 13 | 324.06 | −191.44 |
| T 10 | 670 + 13 | 292.24 | −390.76 |

Conclusions
Colony-Forming Units Per Gram of Leaf (CFU/g of Leaf)

A persistence of microorganisms in leaf is observed throughout the strawberry growing cycle.

Total Nitrogen

Plants treated with *Methylobacterium* sp. nov. strain of the invention in treatment 9 have the highest nitrogen concentration in leaf, compared with all control treatments.

Production

The application of *Methylobacterium* sp. nov. strain of the invention in treatment 9 (503 UFN), promoted an increase in the production of 21% with respect to the control Treatment 5 (671 UFN) and an increase of 33% with respect to its homologue fertilized Treatment 4 (503 UFN).

Example 5

Trial 5—Field Validation Trial in the Vine Culture
Objective.

To know the efficacy of the strain of the invention on the development of the culture of vine, subjected to a conventional dose of nitrogen fertilization, through the evolution of the green color of the leaf (SPAD), concentration of the microorganism in the leaf and the production yield.

Materials and Methods

Trial Fields and Fertilization.

The trial was carried out in two fields, located in Jumilla, with coordinates 38° 33'13.9"N 1° 21'16.5"W, and Tomelloso, with coordinates 39° 11'22.4"N 2° 59'15.8"W.

Fertilization recommendations were conventional fertilization with background fertilization with 700 kg NPK (15-15-15), corresponding to 105 UFN for the entire culture cycle.

Distribution of the Treatments in the Fields.

The fields had the following surface: Field 1 (1 ha), Field 2 (2.20 ha) and two adjacent 16 meter wide blocks (i.e., areas) were taken for the evaluation of the parameters.

Characteristics of the Culture and Application of *Methylobacterium* sp. Nov. Strain of the Invention In Field 1 the vine variety is petit verdot in Field 2 the variety is Grenache, the application date of the strain of the invention was on 10 May 2018 (Field 1) and 15 May 2018 (Field 2).

The *Methylobacterium* sp. nov. strain of the invention was applied at a dose of 333 g/ha ($3 \times 10^7$ CFU/g) by foliar application.

The foliar application was carried out with a nebulizer with 350 liters of broth per hectare when the plant was in the peppercorn stage with an air temperature of 17 and 20° C. and a relative humidity of 20 and 38%, with a speed of wind of 5.4 and 9 mps south and northwest direction, without presence of dew on the leaves and a cloudiness of 10 and 25% respectively.

Figure 12A:
FIG. 12A shows the nebulizer at the time of application of the treatment(s) and FIG. 12B shows the grain size at the time of application of the treatment(s).
Figure 12B:
Figure 13:
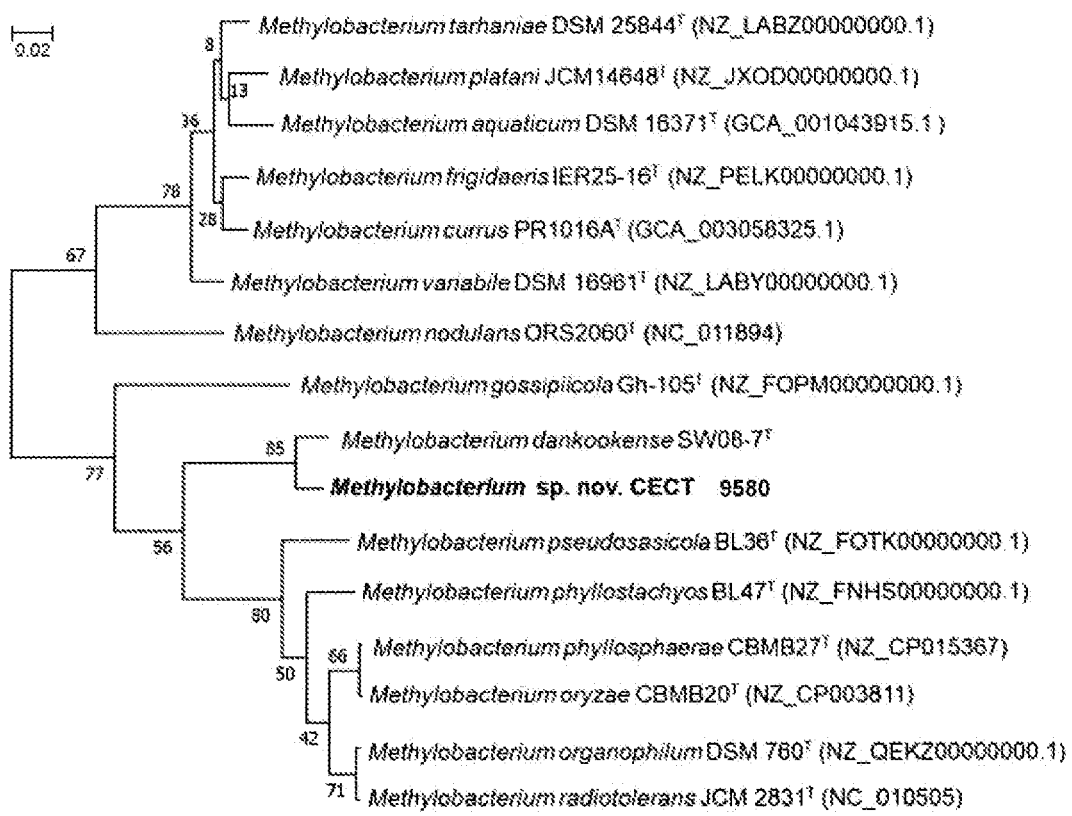
FIG. 13 shows a phylogenetic tree generated with UBCG by using amino acid sequences. The numbers at the nodes indicate the gene support index (maximal value is 92). Genome accession numbers are indicated in parentheses. Bar, 0.05 substitutions per position.

FIG. 12A shows the nebulizer at the time of application of the treatment(s) and FIG. 12B shows the grain size at the time of application of the treatment(s).

Parameters and Evaluation Methodology
Yield

To evaluate the yield of the crop, 6 blocks are taken at random and 30 square meters of surface are harvested, weighing the grapes obtained in the plants.

Statistical Analysis.

The factor (yield) and their interaction were analyzed for each parameter by ANOVA, using Statgraphics Plus software for Windows 5.1 (Manugistics, Inc., USA).

Results
Yield

Table 19A and Table 19B, here below reported, shows results concerning yield in kilograms per plant for each treatment.

TABLE 19A

| | Field 1 | | |
|---|---|---|---|
| Tretament | Total weight (kg/pl) | ° Brix | Kg/ha |
| Treated | 6.02 | 24.8667 | 16464 |
| Control | 5.09 | 24.5778 | 13937 |

TABLE 19B

| | Field 2 | | |
|---|---|---|---|
| Treatment | Total weight (kg/pl) | ° Brix | Kg/ha |
| Treated | 19.77 | 17.5 | 49440 |
| Control | 14.02 | 18 | 35065 |

Conclusion

In the Field 1, the application of *Methylobacterium* sp. now. strain of the invention could increase the yield in a 18% respect to the untreated control.

In the Field 2, the application of *Methylobacterium* sp. nov. strain of the invention could increase the yield in a 41% respect to the untreated control.

Example 6

Trial 6—Evaluation of the Effects of *Methylobacterium* sp. Nov. Strain of the Invention on the Yield on Escarole Crop (*Cichorium endivia latifolia*, Variety Lempika)

The following test was carried out by an independent accredited entity for the realization of GEP trials.

The design, analysis of results and reporting of this study were carried out following whenever possible the EPPO-Guidelines PP 1/152(4), PP 135(4) and PP 1/181(4).

General Information of the Trial

The trial began on 17 Aug. 2018 in Vila-Sacra, province of Gerona in Spain, ending on 12 November of the same year. The date of the transplant was 21 Aug. 2018. Conventional fertilization was performed on 23 August and the application of the *Methylobacterium* sp. nov. strain of the invention was on 28 September, once the culture has reached the suitable stage of development (BBCH 17-19).

Design of the Trial

The trial consisted of a randomized block system with 4 treatments and 5 replications. Each elementary field (plot) was 2.5 meters wide and 7 meters long, with an area of 17.5 m². The rows of plants were 0.56 meters spaced apart and the space in the row was 0.35 m giving rise to a total of 80 plants in 4 rows.

Culture

The effect of the *Methylobacterium* sp. nov. strain of the invention was studied in the endive crop (*Cichorium endivia latifolia*, variety Lempika). Previous crops in that area were onions in 2018 and sunflower and lettuce in 2017.

Soil

The soil showed a good level of fertilization:
% MO: 2.02
Texture: clay loam
pH: 7.70
CEC: 0.22
Soil drainage: fair Maintenance Throughout the culture cycle, the phytosanitary treatments necessary to maintain plant health were applied.

evaluated and compared to an "untreated" control (with the 100% of N fertilization, but without the *Methylobacterium* sp. nov. strain of the invention).

Fertilization was done before transplant (23 Aug. 2018). The product was applied at BBCH stage 17-19 (28 Sep. 2018), using a calibrated knapsack sprayer HONDA WRJ2525.

Three assessments were done on crop vigor during the crop development as percentage. At harvest or close to harvest it were recorded the yield parameters evaluating the two central rows of the plots, with 20 plants each, and the two border rows were not considered for the assessments. The plant diameter (cm), the number of plants present (distinguishing marketable, unmarketable, dead and chlorotic plants), the plant weight and the yield (number and kg on the 2 central rows (7.84 m²)) were assessed. The yield and the number of marketable plants per hectare and the % of increase versus the treatment without with standard fertilization (treatment 1) was calculated automatically calculated using ARM software. Phytotoxicity and vigor assessments were carried out throughout the trial.

Table 20, here below reported, shows the treatment list

TABLE 20

| Trt No. | Treatment Name | Rate | Rate Unit | Growth Stage | Appl Code | Appl Description |
|---|---|---|---|---|---|---|
| 1 | UTC | | | | | |
|   | UF | 1000 | kg/ha | BEFTRA | A | Before transplant |
| 2 | M.s. | 300 | g/ha | BBCH 16-19 | B | Crop BBCH 16-19 |
|   | UF | 1000 | kg/ha | BEFTRA | A | Before transplant |
| 3 | M.s. | 300 | g/ha | BBCH 16-19 | B | Crop BBCH 16-19 |
|   | F (DOSE N = 60%) | 600 | kg/ha | BEFTRA | A | Before transplant |
| 4 | M.s. | 300 | g/ha | BBCH 16-19 | B | Crop BBCH 16-19 |
|   | F (DOSE N = 40%) | 400 | kg/ha | BEFTRA | A | Before transplant |

Statistical Comments

Statistical analysis and reports have been realized with the software of the Manager of Agricultural Investigation (ARM) (developed by Gylling Dates Management Inc.) The data evaluated was analyzed using a one-way analysis of variance (ANOVA) combined with a Student-Newman-Keuls in α=5% for comparison of means. The means followed by the same letter do not differ significantly.

Objectives of the Trial

1.—To evaluate the effects of the *Methylobacterium* sp. nov. strain of the invention on the crop behaviour and yield on escarole crop, applied with normal rate of fertilization or reduced fertilization.

2.—To compare the effects of the *Methylobacterium* sp. nov. strain of the invention compared to a standard commercial fertilization 3.—To evaluate any unintended effect of the *Methylobacterium* sp. nov. strain of the invention on the target crop.

Trial Summary

The objective of this trial was to evaluate the effects of the *Methylobacterium* sp. nov. strain of the invention, (3×10⁷ CFU/g) when the dose of Nitrogen (fertilization) is reduced, on the yield of escarole crop. The trial was located in Northeast of Spain, in Vila-Sacra municipality (Girona), in open field, in a typical small area for the cultivation of vegetables. The study was conducted in compliance with the principles of Good Experimental Practices as defined by Regulation 1107/2009 of the European Union.

The strain of the invention was tested at the same rate (300 g f.p./ha) in three areas with different Nitrogen fertilization rates (100% (usual), 60% and 40%), and it was In Table 20, the following reference are used:
UTC: Untreated Control
UF: Usual fertilization
F: Fertilization
M.s.: *Methylobacterium* sp. nov. strain, i.e., the *Methylobacterium* sp. nov. strain of the invention Conclusions Effects of the Product According to the trial conditions, it can be concluded that the application of the *Methylobacterium* sp. nov. strain of the invention with a reduced dose of Nitrogen obtained a numerical increase of the mean plant weight (kg) and commercial yield (number of plants per hectare) compared with only one application of conventional fertilizer (without *Methylobacterium* sp. nov. strain of the invention), which means that the *Methylobacterium* sp. nov. strain of the invention provided the necessary nitrogen for a correct development of the plant.

Treatments 3 and 4 achieved a crop yield increase of 3.8 and 13.89% respectively when compared to treatment 1, obtaining significant statistic differences. No significant differences were obtained among the *Methylobacterium* sp. nov. strain of the invention treatments with different doses of Nitrogen in the rest of assessed parameters, despite the obtained results suggested best results at higher Nitrogen reduction.

*Methylobacterium* sp. nov. strain of the invention was applied at dose 300 g/ha (3×10⁷ cfu/g) when crop had between 7 and 9 leaves (BBCH 17-19).

The strain of the invention applied at 300 g/ha (3×10⁷ cfu/g) with conventional fertilization (N=40%) showed the best results of the trial with a yield increase of 13.89%, with statistic significant difference.

Regarding the other parameters assessed, there were not significant statistical differences among treatments, which indicates that the *Methylobacterium* sp. nov. strain of the invention was able to provide the necessary nitrogen for the correct development of the plants.

The use of the *Methylobacterium* sp. nov. strain of the invention reduces the amount of nitrogen fertilization required in the crops since the results of the assessed parameters were similar or even better to those obtained with conventional fertilization.

Example 7—Process for the Production of an Exemplary Composition According to the Invention Recover *Methylobacterium* sp. Nov. Strain NFBG Medium (Nitrogen Free Bacterial Medium Supplemented with Glucose).

Growth parameters:
Growth temperature 20-35° C.
Incubation time 5-7 days.

Select an Isolated Pink-Red Colony and Reseed it in Selective Medium MMMNF (Minimal Medium with Methanol Nitrogen Free).

Growth parameters:
Growth temperature 20-35° C.
Incubation time 5-7 days.

Select an Isolated Colony (Pink-Red) and Reseed it in MMM (Minimal Mineral Medium with Methanol), to Grow a Liquid Culture to be Used as a Pre-Inoculum Fermentation parameters:
Growth temperature 20-35° C.
Agitation (r.p.m.) 50-250.
Fermentation time 5-7 days.

Inoculation of the Complete Volume of the Bioreactor with the Pre-Inoculum of the Microorganism.

Fermentation parameters:
Growth temperature 20-35° C.
Agitation (r.p.m.) 50-250.
Aeration 0.3-3.2 N*m$^3$/h.
Fermentation time 80-130 hours.

Mix with the Carriers and Dry with Spray Drying

Each Liter of Fermented Broth with the Microorganism is Mixed with Agriculturally Acceptable Carriers After the Mixture is Spray Dried, According to the Following Drying Parameters:

Feed flow 7-11 ml/l.
Compressed air flow 225-375 l/h.
Drying air flow 35-50 m$^3$/h.
Entry temperature 100-180° C.
Cyclone performance 25-40%.

Mix of Products for Final Product Formulation

Each 1 g of dry product (powder+microorganism) is mixed with the following co-formulators, until obtaining 101-550 g of final product, to be used in the fertilization of one hectare.

1-50 g agriculturally acceptable co-formulant.
100-500 g agriculturally acceptable carrier.

Table 21, here below reported, shows the composition in g/L of the culture media used throughout the manufacturing process.

TABLE 21

|  | NFM | MMM | MMMNF |
|---|---|---|---|
| Malic acid | 5.0 g | | |
| Methanol (sterilized by filtration 0.22 μm) | 20 ml | 20 ml | 20 ml |
| NaNO$_3$ | | 0.5 g | |
| (NH4)$_2$SO$_4$ | | 0.5 g | |
| (NH4)$_6$Mo$_7$O$_{24}$ 4H$_2$O | 0.002 g | | 0.002 g |
| MgSO$_4$ 7H$_2$O | 0.2 g | 0.5 g | 0.5 g |
| K$_2$HPO$_4$ | 0.1 g | 1.0 g | 1.0 g |
| KH$_2$PO$_4$ | 0.4 g | | |
| FeCl$_3$ | 0.01 g | | |
| FeSO$_4$ 7H$_2$O | | 0.01 g | 0.01 g |
| KCl | | 0.5 g | 0.5 g |
| NaCl | 0.1 g | | |
| CaCl$_2$ 2H$_2$O | | 0.01 g | 0.01 g |
| KOH | 4.8 g | | |
| Sol. Micronutrients | 2.0 ml | 2.0 ml | 2.0 ml |
| Sol. Vitamins (sterilized by filtration 0.22 μm) | 1.0 ml | 1.0 ml | 1.0 ml |
| Bromotimol blue (0.5% sol. in 2 N KOH) | 2.0 ml | | |
| pH | 6.9 | 7.2 | 7.2 |
| Agar-Agar | 12.0 g | | 12.0 g |

Components sterilized by filtration are added after autoclaving, once the culture medium has cooled to a temperature<60° C.

Table 22, here below reported, refers to the amount in grams of the micronutrients and vitamins.

TABLE 22

|  | MICRONUTRIENTS | VITAMINS |
|---|---|---|
| H$_3$BO$_3$ | 1.85 g | |
| MnSO$_4$ 4H$_2$O | 2.45 g | |
| ZnSO$_4$ 7H$_2$O | 0.28 g | |
| Na$_2$MoO$_4$ 2H$_2$O | 0.034 g | |
| CoCl$_2$ 6H$_2$O | 0.005 g | |
| CuSO$_4$ 5H$_2$O | 0.005 g | |
| Nicotinic acid | | 0.2 g |
| Biotin | | 0.0018 g |
| Calcium pantotheate | | 0.18 g |
| Pyridoxine | | 0.18 g |
| Cyanocobalamin | | 0.08 g |
| Thiamin | | 0.2 g |

The invention claimed is:

1. An agricultural composition formulated for foliar application to a plant comprising a strain of *Methylobacterium* sp. nov. deposited under accession number CECT 9580 and a surfactant.

2. A process for the production of a composition according to claim 1, comprising the following steps:
    providing at least one *Methylobacterium* sp. nov. deposited under accession number CECT 9580 according to the invention,
    inoculating *Methylobacterium* sp. nov. in a liquid culture medium including methanol,
    culturing said *Methylobacterium* sp. nov. to obtain a liquid culture comprising *Methylobacteria*, and
    drying said liquid culture to obtain a dry composition.

3. The process according to claim 2, wherein said *Methylobacterium* sp. nov. deposited under accession number CECT 9580 is isolated from the inner of the spores of the mycorrhizal fungus *Glomus iranicum* var. tenuihypharum, deposited under BCCM deposit number 54871.

4. The process according to claim 2, further comprising a step of adding one or more agriculturally acceptable carriers to the liquid culture comprising *Methylobacteria* before drying.

5. The process according to claim 2, further comprising a step of adding one or more agriculturally acceptable co-formulant.

6. The process according to claim 5, wherein said one or more agriculturally acceptable co-formulants are added to said dry composition.

7. A method for reducing up to 60% of nitrogen external input comprising using the *Methylobacterium* sp. nov. strain according to claim 1 by applying the strain to plants.

8. A method of treating plants, comprising applying the composition according to claim 1 as a bio-stimulant to plants.

9. The method according to claim 8, wherein said plants are horticultural crops, extensive herbaceous and gramineous crops, wood crops as grapevine, berries, and legumes.

10. The method according to claim 8, for wherein applying the strain as bio-stimulant increases the yield of said plants.

11. The agricultural composition of claim 1, further comprising an agriculturally acceptable carrier.

12. The agricultural composition of claim 11, wherein the agriculturally acceptable carrier is selected from the group consisting of:

(i) a solid particulate carrier;
(ii) an aqueous liquid carrier;
(iii) an oil dispersion carrier;
(iv) an oil-in-water or water-in-oil emulsion stabilized with at least one emulsifier;
(v) a semi-solid carrier comprising a hydrocolloid gel; and
(vi) a gel matrix.

13. The agricultural composition of claim 1, further comprising an agriculturally acceptable adjuvant, agriculturally acceptable excipient, a pesticide, a bacteriostatic agent, a biopesticidal microorganism, or a plant beneficial microorganism.

14. The agricultural composition of claim 1, wherein the composition is (a) a solid powder; (b) an aqueous liquid; (c) an oily form; (d) an emulsion; (e) a semi-solid; or (f) a gel.

15. The agricultural composition of claim 1, formulated for application by foliar spray.

16. The agricultural composition of claim 1, further comprising one or more agriculturally acceptable co-formulants.

17. An agricultural composition comprising a seed, a strain of *Methylobacterium* sp. nov. deposited under accession number CECT 9580, and a surfactant.

* * * * *